(12) United States Patent
Rekker et al.

(10) Patent No.: US 8,778,832 B2
(45) Date of Patent: *Jul. 15, 2014

(54) FISCHER-TROPSCH CATALYST

(75) Inventors: Tjalling Rekker, Culemborg (NL); Cornelis Roeland Baijense, Gameren (NL)

(73) Assignee: BASF Corporation, Florham Park, NJ (US)

( * ) Notice: Subject to any disclaimer, the term of this patent is extended or adjusted under 35 U.S.C. 154(b) by 855 days.

This patent is subject to a terminal disclaimer.

(21) Appl. No.: 12/268,908

(22) Filed: Nov. 11, 2008

(65) Prior Publication Data

US 2009/0197981 A1 Aug. 6, 2009

(30) Foreign Application Priority Data

May 1, 2006 (EP) .................. 060759727

(51) Int. Cl.
| | | |
|---|---|---|
| C07C 27/10 | (2006.01) | |
| B01J 23/80 | (2006.01) | |
| B01J 23/10 | (2006.01) | |
| C07C 29/141 | (2006.01) | |
| C10G 2/00 | (2006.01) | |
| B01J 35/02 | (2006.01) | |
| B01J 37/03 | (2006.01) | |
| B01J 21/06 | (2006.01) | |
| B01J 35/10 | (2006.01) | |
| B01J 23/889 | (2006.01) | |
| B01J 23/89 | (2006.01) | |
| B01J 23/83 | (2006.01) | |

(52) U.S. Cl.
CPC ............... *C07C 29/141* (2013.01); *B01J 21/06* (2013.01); *B01J 35/1014* (2013.01); *B01J 35/1009* (2013.01); *C10G 2/332* (2013.01); *B01J 35/1038* (2013.01); *B01J 35/1019* (2013.01); *B01J 23/8896* (2013.01); *B01J 35/1061* (2013.01); *B01J 23/8953* (2013.01); *B01J 21/066* (2013.01); *B01J 35/023* (2013.01); *B01J 37/03* (2013.01); *B01J 23/83* (2013.01); *B01J 35/1066* (2013.01); *B01J 23/80* (2013.01)

USPC ........... 502/329; 502/303; 502/304; 502/326; 502/327; 502/331; 502/332; 502/333; 502/334; 502/339; 502/342; 502/346; 502/349

(58) Field of Classification Search
CPC ........ B01J 23/575; B01J 23/80; B01J 35/002; B01J 35/023; B01J 35/026; B01J 35/1009; B01J 35/1019; B01J 35/1014; B01J 35/1038; B01J 37/03; B01J 37/031; C01G 2/332
USPC ......... 502/302–304, 326, 327, 329, 331–334, 502/339, 342, 346, 349
IPC ....................................................... B01J 23/40
See application file for complete search history.

(56) References Cited

FOREIGN PATENT DOCUMENTS

WO WO03/090925 * 11/2003 ............... B01J 23/40

* cited by examiner

*Primary Examiner* — Jun Li
(74) *Attorney, Agent, or Firm* — Melanie L. Brown

(57) ABSTRACT

The present invention is directed to a catalyst suitable for catalyzing a Fischer-Tropsch reaction, said catalyst comprising cobalt metal supported on zinc-oxide and having the following particle size distribution by volume: <10% having a particle size below 1 micron, 70-99% having a particle size between 1 and 5 micron, and <20% having a particle size above 5 micron.

9 Claims, No Drawings

FISCHER-TROPSCH CATALYST

The invention relates to a Fischer-Tropsch catalyst comprising cobalt and zinc, as well as to a method for preparing such a catalyst.

A catalyst containing cobalt oxide and zinc oxide for use in the synthesis of $C_1$-$C_3$ aliphatic hydrocarbons is known from U.S. Pat. No. 4,039,302.

U.S. Pat. No. 4,826,800 describes a process for preparing a catalyst comprising cobalt and zinc oxide for use after reductive activation as a catalyst in the conversion of synthesis gas to hydrocarbons. The catalyst is prepared by mixing a solution of a soluble zinc salt and a soluble cobalt salt with a precipitant such as ammonium hydroxide or ammonium carbonate and recovering the precipitate. The ratio of carbonate to metal is high in the described method, which has been found detrimental to the strength of the catalyst.

U.S. Pat. No. 5,345,005 relates to a Cu—Zn catalyst on alumina for the preparation of alcohols by hydrogenation of e.g. a ketone. In a comparative example, the preparation of a Cu—Zn—Co catalyst on alumina is described, wherein use is made of soda ash. However, the use of soda ash is found to be potentially detrimental to the strength of the catalyst. The particle size distribution range within which 90% of the volume of the Cu—Zn—Co catalyst described in U.S. Pat. No. 5,345,005 lies, is not specified. It is however expected that the use of soda ash in the preparation of the catalyst leads to a broadening of the particle size distribution.

U.S. Pat. No. 5,945,458 and U.S. Pat. No. 5,811,365 describe a Fischer-Tropsch process in the presence of a catalyst composition of a group VIII metal, e.g. cobalt, on a zinc oxide support. Such a catalyst is made by first preparing the support by adding a solution of zinc salt and other constituents to an alkaline bicarbonate solution. Next, the precipitate is separated from the bicarbonate solution by filtration to form a filter cake, which can thereafter be dried, calcined and loaded with the group VIII metal. The catalyst material is then formed into tablets, which tablets are crushed to form particles with a size of 250-500 μm, that can be used in a Fischer-Tropsch process. Additional post-treatments such as crushing, are required in order to obtain a catalyst powder with good strength properties. However, the obtained average particle size, as indicated above, is still relatively large. Moreover, crushing results in a broad particle size distribution and catalysts with such a large particle size and a broad particle size distribution tend to be less suitable for processes involving a bubble column, a slurry phase reactor or a loop reactor.

WO-A-01/38269 describes a three-phase system for carrying out a Fischer-Tropsch process wherein a catalyst suspension in a liquid medium is mixed with gaseous reactants in a high shear mixing zone, after which the mixture is discharged in a post mixing zone. Thus mass transfer is said to be enhanced. As suitable catalysts inter alia cobalt catalysts on an inorganic support, such as zinc oxide are mentioned. The surface area of the support used for the preparation of these known catalysts is less than 100 g/m². These prior art cobalt based catalysts can be prepared by depositing cobalt on a suitable support, such as a zinc oxide support, by impregnation methodology. Other conventional preparation methods include precipitation routes, which typically involve crushing of a hard filter cake of catalyst material, resulting from the catalyst preparation process, into small particles.

WO-A-03/090925 describes a catalyst comprising particles of a cobalt and zinc co-precipitate, said particles having a volume average particle size of less than 150 μm and a particle size distribution wherein at least 90% of the volume of the catalyst particles have a size between 0.4 and 2.5 times the average particle size. Although this catalyst is an improvement over the previously known catalysts, there is still room for improvement, especially with respect to the balance of properties required between the properties needed during activation on the one hand and attrition and activity properties during FT operation on the other hand.

In the case of slurry-phase Fischer Tropsch catalysts, always a good balance should be adjusted between activity (Fischer Tropsch performance) and separation properties. In that respect, the (powder) catalyst should have an optimized particle size distribution giving good mass-transfer and separation properties. These properties should not change substantially during time on stream in the process so that activity and separation properties are retained over long periods of time.

Prior art supported cobalt catalysts for Fischer Tropsch are generally based on a mechanically strong support that is impregnated with a cobalt solution and subsequently dried, calcined and reduced. Alternatively, a mechanically strong cobalt-support system can be precipitated by optimizing the precipitation conditions. Such formulations are mechanically stable in both the fluid-bed catalyst activation and the slurry-phase Fischer Tropsch reactor, although attrition in the Fischer Tropsch reactor may lead to fines (submicron particles) formation and consequently separation problems. The preferred particle size distribution to achieve good fluidization behaviour during fluid-bed activation is generally different from the required, preferred particle size distribution for the Fischer Tropsch process. The chosen particle size distribution of the fresh catalyst always forms a compromise between the two.

The invention is based thereon that a (coprecipitated) Fischer-Tropsch catalyst based on cobalt on zinc-oxide having a very specific particle size distribution, has a very good balance of properties, especially with respect to behaviour during activation and during use.

The catalyst of the invention is accordingly defined by the following particle size distribution by volume:
<1.0% having a particle size below 1 micron,
70-99% having a particle size between 1 and 5 micron, and
<20% having a particle size above 5 micron.

Surprisingly it has been found that a Fischer Tropsch (FT) catalyst comprising cobalt metal supported on zinc-oxide and meeting the above, relatively broad particle size distribution fulfils the requirements for a good FT-catalyst in that it has good activation properties, that it has a strong attrition resistance during operation, that it has good filtration properties and that it has a good performance.

In a preferred embodiment, the particle size distribution by volume is as follows:
<10% having a particle size below 1 micron,
75-95, more preferred 75-85% having a particle size between 1 and 5 micron, and
<15% having a particle size above 5 micron.

The specific particle size distribution of the catalyst of the present invention may further be defined on the basis of the ratio of the width of the particle size distribution curve at half the height of the peak of the distribution curve and the D50 (vol. %/micron). This value is preferably at least 0.85, and more preferred at least 0.90.

The volume average particle size and particle size distribution have been determined by the so-called Fraunhofer diffraction method. Analyses were performed on a Sympatec HELOS Laser Diffraction apparatus, equipped with a SUCELL automated wet dispersing unit, equipped with a small volume adapter (SVA). Measurements were done in tetradecene, where the measuring procedure contains the following parameters; measurement particle size range 0.25-87.5 μm, measuring duration 20 sec. and cycle-time 100 msec., see also Examples. No ultrasonic treatment was applied prior to the measurement.

A catalyst according to the invention has been found to have a particular good mass and/or heat transfer properties, when used in a catalytic process.

A catalyst according to the invention has been found to be particularly favourable for use in a stirred slurry-phase reactor, bubble-column reactor, loop reactor or fluid-bed reactor.

A catalyst according to the invention shows very favourable separation properties and can for example very suitably be separated from the reaction mixture by filtration.

A catalyst according to the invention has an extremely good balance between activity and separation properties Preferably the volume average particle size of the catalyst is less than 50 μm, more preferably less than 25 μm. The lower limit is not particular critical, provided it meets the criteria of the invention. For practical purposes it is preferred that the size is at least such that the particles can still be separated from a liquid reaction mixture. Particularly suitable is for example a catalyst with a volume average particle size of 2 μm or more. Very good results have been achieved with a catalyst having a volume average particle size in the range of 1.6-15 μm.

Preferably the pore volume of the catalyst—as determined by nitrogen adsorption (N2-BET, measured on an Ankersmit Quantachrome Autosorb-6 apparatus, after degassing the sample at 180° C. to a pressure of 3.3 Pa (25 m Torr)—is at least mainly formed by pores having a diameter in the range of 5-100 nm. Much preferred wherein there are essentially no pores with a diameter of less than 5 nm (in particular less than 5% of the pore volume formed by pores with a diameter of less than 5 nm). It has been found that such a catalyst has particularly good diffusion properties for reactant and product. Such a catalyst has also been found to be highly selective towards the Fischer-Tropsch reaction.

Very good results have been achieved with a catalyst having a pore volume of less than 0.5 ml/g. The pore volume is preferably at least 0.05 ml/g. Particularly suitable is a catalyst with an pore volume of less than 0.45 ml/g.

Such a catalyst has been found to have particularly good physical strength properties, which is advantageous in applications in various types of reactors, including slurry-phase reactors, loop-reactors, bubble-column reactors and fluid-bed reactors.

The catalyst of the invention is based on cobalt on zinc oxide. The composition of the catalyst can be varied widely, which composition the skilled professional will know to determine, depending upon the intended purpose. Preferably, the zinc to cobalt atomic ratio is in the range of 75 to 0.1, preferably of 40 to 0.1 and more preferably in the range of 20 to 0.3.

The catalyst may essentially consist of cobalt and zinc oxide. It is however also possible that the catalyst contains one or more other components, such as components that are commonly employed in Fischer-Tropsch catalysts. For example the catalyst may contain one or more promoters, such as ruthenium, hafnium, platinum, zirconium, palladium, rhenium, cerium, lanthanum or a combination thereof. When present, such promoters are typically used in a cobalt to promoter atomic ratio of up to 10:1.

It has been found that a catalyst according to the invention comprising at least one compound of a group IIIa element, such as an oxide, preferably in a concentration of 0.1-60, more preferably 0.1-10 wt % based upon the total weight of the catalyst, has a very favourable structural stability. Preferred group IIIa elements include aluminium (Al), gallium (Ga) and borium (B), of which aluminium is particularly preferred.

Very good results have been obtained with a catalyst according to the invention which is essentially free of sodium. It has been found that a catalyst containing a relatively high amount of sodium is reduced in strength. Further, the presence of sodium has been found to be detrimental to the activity of the catalyst, reducing its Fischer-Tropsch activity. Therefore, a catalyst with a sodium content of less than 0.5 wt. %, more in particular of 0 to 0.15 wt. %, even more in particular of 0 to 0.1 wt. % based upon the weight of the catalyst, is preferred.

Very good results have been achieved with a catalyst according to the invention having a low content of copper or being essentially free of copper. Copper may stimulate side reactions, such as the formation of an alcohol by hydrogenation of a ketone, an aldehyde or a carboxylic acid, which are usually preferably avoided or suppressed, especially in a Fischer-Tropsch process. The copper content is preferably less than 2 wt. %, more preferably 0 to 0.5 wt % even more preferably 0 to 0.2 wt. %, based upon the weight of the catalyst.

The preparation of the catalyst of the present invention comprising cobalt and zinc oxide, can be done by co-precipitation of cobalt and zinc ions.

In order to produce the catalyst with the specific structure, various options are available.

A very suitable method is based on the method described in WO 03/090925, whereby the process is modified in such a way that the structure of the present invention is obtained. This can, for example, be done by changing the stirring speed or the rate of injection of the solution(s) in the reaction vessel or by applying other types of agitation. As the particles of the catalyst of the present invention are generally smaller and have a different particle size distribution, compared to said document, higher stirring speeds, shorter contact time and/or higher injection speeds are preferred.

In the alternative, one may produce first particles that are within the ranges of WO 03/0.90925 following which the particles are comminuted to obtain the catalyst of the invention, for example by ultrasonic treatment or another comminuting treatment.

Generally the process comprises a coprecipitation method, wherein an acidic solution comprising zinc ions and cobalt ions and an alkaline solution are supplied to a reactor comprising an aqueous medium, preferably water or an aqueous solution, wherein the acidic solution and alkaline solution are contacted in the aqueous medium and a precipitate comprising cobalt and zinc is formed. The precipitate is thereafter separated from the aqueous medium (which may have formed a slurry together with the precipitate). The separated cobalt and zinc comprising precipitate is then dried and may be post-treated, e.g. calcined, etc, to form said catalyst.

The combination of acidic solution and alkaline solution is preferably chosen such that the components of the acidic solution and of the alkaline solution are soluble in the aqueous medium, but that the cobalt and zinc precipitate when they are contacted with the alkaline solution, while the counter ions of zinc and cobalt substantially remain in solution. The skilled professional will know how to choose appropriate conditions, such as the type of counter ions and the concentrations for each of the components.

This method has been found to be particularly suitable for preparing a catalyst as described above.

It has been found that a method according to the invention allows the direct preparation of a particulate precipitate that acts as a free flowing catalyst precursor, directly after drying, i.e. it allows the preparation of a precipitate that does not have to be crushed or otherwise mechanically treated to form a particulate material. It is, however, possible to design the process in such a way that first a material is prepared that afterwards can be converted to the final catalyst by comminution.

Preferably the precipitation of particles is carried out at a substantially constant pH, in particular at a pH value varying at most ±0.2 pH units around a set-point value. Thus it has been found possible to make a catalyst precursor with very favourable free flowing characteristics and good mechanical strength properties.

Preferably, the alkaline solution and the acidic solution are supplied to the reactor simultaneously (from separate conduits).

Optionally the cobalt in the isolated and dried precipitate or calcined product is reduced to metallic cobalt Suitable sources for ionic zinc respectively ionic cobalt include salts thereof that are soluble in the acidic solution and in water in a sufficient concentration. Preferred examples of such salts include zinc nitrate respectively cobalt nitrate and zinc acetate respectively cobalt acetate and other inorganic or organic salts of cobalt respectively zinc that have a similar solubility in the acidic solution Suitable components for co-precipitating with the cobalt ions and 65 zinc ions present are inorganic salts and organic salts that are soluble in an aqueous alkaline solution in a sufficient concentration, such as hydroxides, carbonates, urea, isocyanates and any other salt that can be used as base source and that can be dissolved water of in the alkaline solution. Preferred examples of such salts include ammonium carbonate, ammonium bicarbonate and other inorganic or organic salts of carbonate that have at least a similar solubility in the alkaline solution.

Preferably the total concentration of zinc and cobalt ions in the aqueous medium is chosen in the range of 0.1 to 5 moles/liter. The concentration is preferably kept within this range throughout the precipitation step.

The pH of the acid solution is preferably in the range of 1-5. The pH of the alkaline solution is preferably in the range of 6-14. The pH in the aqueous medium (wherein the co-precipitation takes place) is preferably in the range of 4-9, depending upon the type of precursor salts used as a source for cobalt, zinc and alkaline component(s).

The stirring frequency is very suitably chosen to obtain a power input in the range of 1-300 kW/l aqueous medium. Very good results have been achieved with a power input in the range of 10-100 kW/l aqueous medium.

The temperature during the co-precipitation process is preferably chosen in the range of 5-98° C., more preferably in the range of 15-75° C.

The present invention further relates to the use of a catalyst according to the invention in a slurry reactor, a loop reactor, a bubble-column reactor or a fluid-bed reactor. The present invention further relates to the use of a catalyst according to the invention in a Fischer-Tropsch process or a functional group hydrogenation process, such as nitrite hydrogenation to amines.

The invention is further illustrated by the following examples.

EXAMPLE 1

Catalyst Preparation

20% Co/ZnO Catalyst.

23.4 kg $Zn(NO_3)_2 \cdot 6H_2O$ and 8.3 kg $Co(NO_3)_2 \cdot 6H_2O$ were dissolved in 80 liter water. A separate solution was made consisting of 11.68 kg ammonium carbonate in 80 liter water. Both solution were simultaneously pumped into a heel of water (130 liter), while stirring the solution at 75° C. After completion the precipitation process, an extra amount of ammonium carbonate solution was added to increase the final pH to 7.1.

After completing the precipitation process, the precipitate was transferred to a filter press and extensively washed until ammonium- and nitrate-free. The filter cake was subsequently dried in a flash dryer and calcined for 5 hours at 50000.

2.5 kgs of the calcined catalyst precursor were loaded into a fluid-bed reactor and reduced in a stream of 25% hydrogen in nitrogen. The reduction was carried out for 6 hours at 335° C. After completion of the reduction, the fluid-bed unit was unloaded into a slurry-phase Fischer Tropsch loop-reactor, which was filled with wax as the reaction medium. Particle size distribution analysis showed a breakdown of the initial particles in the first 30 hours on stream, whereby the average particles size decreased from 24.9 μm to 2.6 μm. The catalyst showed excellent Fischer Tropsch performance, while retaining also good separation behaviour during the Fischer Tropsch run.

EXAMPLE 2

Measurement of the Particle Size Distribution

The volume average particle size and particle size distribution have been determined by the so-called Fraunhofer diffraction method. Analyses were performed on a Sympatec HELOS Laser Diffraction apparatus. A representative sample of catalyst, dispersed in tetradecene, was loaded into the small volume adapter (SVA) of the SUCELL dispersing unit, and measurements were performed with the following settings: measurement particle size range 0.25-875 μm, measuring duration 20 sec. and cycle-time 100 msec. Stirrer speed and pump speed were adjusted at 600% and 70%, respectively. No ultrasonic treatment was applied prior to, or during, the measurements. Particle size distribution was calculated as a volume distribution.

EXAMPLE 3

Catalytic Performance of Catalyst in Fischer-Tropsch Reaction

A catalyst with a cobalt content of 20 wt. % was prepared. The preparation conditions and the particle size distribution of the catalyst were the substantially the same as in Example 1.

A sample of catalyst (20 g) was reduced in a 3.5 cm OD tubular reactor. The reactor was purged with nitrogen at a space velocity (GHSV) of 1000 h-1 at atmospheric pressure. The temperature was raised at 2° C./min to 60° C. The gas feed was then switched over to air at 1000 GHSV. The temperature was then raised at 1° C./min up to 250° C. and held there for 3 hours. The gas flow was then changed to nitrogen at 1000 GHSV for 6 minutes and then the feed gas was switched to carbon monoxide at 1000 GHSV and held for 3.5 hours.

The feed gas was then changed back to nitrogen and the temperature ramped at 4° C./min up to 280° C. Once at 285° C., the feed gas was then switched to hydrogen at 2,500 GHSV and held there for 10 hours. The reactor was then cooled to room temperature and purged with nitrogen-prior to transfer to the reactor.

The catalyst was transferred under nitrogen purge to a 600 ml continuous stirred tank reactor (CSTR) that had been filled with squalane (300 ml, Aldrich). The reactor was sealed and heated up to 125° C. with a nitrogen flow of 250 ml/min. The feed gas to the reactor was then switched to syngas at 8000 GHSV, the stirrer speed increased to 700 rpm and the temperature ramped at 2° C./min up to 130° C. The reactor was then pressurised to 20 barg at 30 bar/hr. The temperature was then ramped at 60° C./hour up to 160° C., 5° C./hour up to 175, 1° C./hour up to 185, 0.5° C./hour up to 205° C. and 0.3° C. hour up to 212° C. Automatic temperature control was then used to maintain the % CO conversion at 60%.

After 40 hours on stream a C5+ productivity of 608 g/liter of catalyst/hr was obtained at a temperature of 226° C.

The invention claimed is:

1. A catalyst suitable for catalyzing a Fischer-Tropsch reaction, said catalyst comprising cobalt metal supported on zinc-oxide and having the following particle size distribution by volume:
   <10% having a particle size below 1 micron, 75-85% having a particle size between 1 and 5 micron, and 15% having a particle size above 5 micron.

2. Catalyst according to claim 1, wherein the volume average particle size is less than 25 μm.

3. Catalyst according to claim 1, wherein the pore volume is mainly formed by pores having a diameter within the range of 5-100 nm.

4. Catalyst according to claim 1, wherein the pore volume is less than 0.5 ml/g.

5. Catalyst according to claim 1, wherein the surface area is less than 120 m$^2$/g.

6. Catalyst according to claim 1, wherein the zinc to cobalt atomic ratio is in the range of 75 to 0.1.

7. Catalyst according to claim 1, wherein one or more promoters, such as ruthenium, hafnium, platinum, zirconium, palladium, rhenium, cerium, lanthanum or a combination thereof are present, typically in a cobalt to promoter atomic ratio of up to 10:1.

8. Catalyst according to claim 1, further comprising at least one group compound of a Ma element, in a concentration of 0.1-0.60 wt %, based upon the total weight of the catalyst.

9. A method for performing a Fischer-Tropsch process, comprising:
   contacting the catalyst of claim 1 with syngas; and recovering a product containing 5 or more carbon atoms.

* * * * *